United States Patent [19]

Pilgram

[11] 4,226,612

[45] Oct. 7, 1980

[54] CERTAIN HERBICIDAL (2-OXO-3-OXAZOLIDINYL)PHENYLUREAS

[75] Inventor: Kurt H. Pilgram, Modesto, Calif.

[73] Assignee: Shell Oil Company, Houston, Tex.

[21] Appl. No.: 54,395

[22] Filed: Jul. 2, 1979

[51] Int. Cl.$^3$ .................. C07D 263/24; C07D 263/38; A01N 43/76

[52] U.S. Cl. ........................................ 71/88; 548/231

[58] Field of Search ............................ 548/231; 71/88

[56] References Cited

U.S. PATENT DOCUMENTS

| | | | |
|---|---|---|---|
| 3,741,977 | 6/1973 | Boesch | 548/144 |
| 4,150,029 | 4/1979 | Dostert et al. | 548/231 |

*Primary Examiner*—Jose Tovar

[57] ABSTRACT

Certain N'-(3-halo-4-(oxazolidinyl)phenyl)-N-alkyl-N-alkyl(oxy)ureas, and their use as herbicides.

3 Claims, No Drawings

CERTAIN HERBICIDAL (2-OXO-3-OXAZOLIDINYL)PHENYLUREAS

DESCRIPTION OF THE INVENTION

It has been found that useful herbicidal properties are possessed by ureas described by the formula:

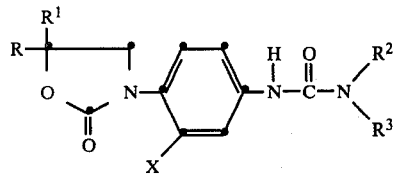

wherein R and $R^1$ each is hydrogen or lower alkyl, $R^2$ is lower alkyl and $R^3$ is lower alkyl, lower alkoxy, or 2-propenyloxy, and X is middle halogen.

In these compounds, each alkyl and alkyloxy moiety contains from one to six carbon atoms and suitably is either straight-chain or branched-chain in configuration.

Typical exemplary individual species of this class of compounds, the manner in which they can be prepared and isolated, and summaries of the results of their herbicidal testing, are set forth in the Examples, hereinafter. Other, typical, individual species are the following (in which the symbols refer to Formula I):

| R | $R^1$ | X | $R^2$ | $R^3$ |
|---|---|---|---|---|
| —$CH_3$ | H | —Cl | —$CH_3$ | —$OCH_3$ |
| —$C_2H_5$ | —$CH_3$ | —Cl | —$CH_3$ | —$OCH_3$ |
| —$C_2H_5$ | —$CH_3$ | —Cl | —$CH_3$ | —$CH_3$ |
| —$C_2H_5$ | —$C_2H_5$ | —Cl | —$CH_3$ | —$OCH_3$ |
| —$C_2H_5$ | —$C_2H_5$ | —Br | —$CH_3$ | —$OCH_3$ |
| H | H | —Br | —$CH_3$ | —$OCH_3$ |
| —$C_2H_5$ | —$C_2H_5$ | —Cl | —$CH_3$ | —$CH_3$ |
| H | H | —Br | —$CH_3$ | —$CH_3$ |
| H | H | —Cl | —$CH_3$ | —$CH(CH_3)_2$ |
| H | H | —Cl | —$CH_3$ | —$C_2H_5$ |

Because of their activity, compounds of Formula I wherein alkyl is methyl and alkyloxy is methoxy are preferred. By "middle halogen" is meant bromine or chlorine.

The compounds of Formula I can be prepared by two general methods:

(1) The appropriate 3-(4-amino-2-X-phenyl)-2-oxazolidinone is treated with the appropriate carbamoyl chloride, $R^2R^3C(O)Cl$.

(2) The appropriate 3-(4-isocyanato-2-X-phenyl)-2-oxazolidinone is treated with the appropriate amine, $R^2R^3NH$.

In the first method, the precursor is treated with the carbamoyl chloride in the presence of a molar equivalent of a tertiary amine (an N,N-dialkylaniline, trimethylamine, triethylamine, ethyldiisopropylamine, pyridine or collidine) optionally in an anhydrous solvent, such as ether, tetrahydrofuran, dioxane, benzene, or toluene, at room temperature or somewhat above—for example, up to 80° C.—to give the desired Formula I compound.

The precursor can be prepared by reducing the appropriate 3-(2-X-4-nitrophenyl)-2-oxazolidinone with (a) hydrogen and a catalyst, such as Raney nickel, palladium or palladium-on-charcoal, the hydrogen being at atmospheric pressure or somewhat above; (b) finely divided iron, zinc, or tin, in an aqueous acidic medium (acetic acid is often suitable) or (c) zinc/aluminum amalgm.

The nitrophenyloxazolidinone can be prepared by treating the appropriate 2-anilinoethanol with phosgene, according to the method of Cornforth in "Heterocyclic Chemistry", R. C. Elderfield, ed., vol. 5, p. 396 (1957).

The nitrophenyloxazolidinone intermediate also can be prepared by (a) treating the appropriate 2-chloroethyl phenylcarbamate with aqueous potassium hydroxide. This method is described at page 398 of the Cornforth reference, supra, and references cited therein. The 2-chloroethyl phenylcarbamate can be prepared by treatment of the appropriate 2-X-4-nitrophenyl isocyanate with 2-chloroethanol, this being a particular application of the general procedure for preparing urethanes by the reaction of isocyanates with alcohols, or (b) by treating a 2-oxazolidinone with the appropriate 1-chloro-2-X-4-nitrobenzene in the presence of a strong base, such as sodium hydride, in a solvent such as dimethylformaide or dimethyl sulfoxide.

In the second method, the treatment is conveniently carried out by adding the isocyanate precursor to an excess of the amine, in a solvent such as ether, at room temperature or somewhat above.

The isocyanate precursor can be prepared by treating the appropriate 3-(4-amino-2-X-phenyl)-2-oxazolidinone with an excess of phosgene, in a solvent such as toluene, and refluxing the resulting mixture.

Referring to specific compounds that can be used in preparing compounds of Formula I, 2-chloroethanol, 1-chloro-2-propanol, 3,4-dichloronitrobenzene, 2-chloro-4-nitrophenyl isocyanate, N-hydroxyurethane and 2-oxazolidinone are commercially available. 1-chloro-2-methyl-2-propanol can be prepared from isobutylene and chlorourea in the presence of calcium carbonate, following the procedure described by A. A. Petrov, J. Gen. Chem. (U.S.S.R.), 15, 690–698 (1945); Chem. Abst., 40, 5698 (1946). O-allyl-N-methylhydroxylamine can be prepared by alkylation of N-hydroxyurethane with allyl bromide, followed by N-methylation with methyl iodide and hydrolysis/decarboxylation.

The preparation of typical, exemplary individual species of the compounds of Formula I are shown in the following examples. In each case, the identity of the product, and of each intermediate involved, was confirmed by appropriate elemental and spectral analyses.

EXAMPLE 1

N'-(3-chloro-4-(2-oxo-3-oxazolidinyl)phenyl)-N-methoxy-N-methylurea (1)

50.0 g of 2-chloro-4-nitrophenyl isocyanate was added, with stirring, to 100 g of 2-chloroethanol. After 2 minutes, the temperature of the mixture rose to 65° C. The mixture then was heated at 80°–90° C. for 10 minutes, and cooled. 200 ml of ether and 200 ml of hexane were added, the mixture was cooled to 15° C. and filtered. Drying of the filter cake gave 2-chloroethyl (2-chloro-4-nitrophenyl)carbamate (1A), as a white solid, mp: 128°–130° C.

A solution of 11.25 g of sodium methoxide in 50 ml of methanol was added drop-by-drop to a stirred solution of 58.0 g of 1A in 400 ml of ethanol. The mixture was refluxed for 5 minutes, then the volatile materials were evaporated under reduced pressure. The residue was treated with water and extracted with ether. The extract was dried and concentrated under reduced pressure. The residue was cooled and filtered to give 3-(2-chloro-4-nitrophenyl)-2-oxazolidinone (1B), as a white solid, mp: 94°–96° C.

A mixture of 24.1 g of 1B and 0.5 g of 10% palladium-on-charcoal catalyst in 150 ml of tetrahydrofuran was treated with hydrogen in a Parr shaker. The mixture then was filtered to give 3-(4-amino-2-chlorophenyl)-2-oxazolidinone (1C) in solution in the tetrahydrofuran.

10.1 g of triethyamine was added to the solution of 1C, then 13.6 g of N-methoxy-N-methylcarbamoyl chloride was added drop-by-drop. After 12 hours at room temperature, the mixture was washed with water and extracted with ether. The extract was dried and the ether was evaporated under reduced pressure. The residue was chromatographed over silica gel to give 1, as a white solid, mp: 151°–153° C.

1B also was prepared as follows:

3.75 g of sodium hydride (57% in oil) was added to a solution of 13.57 g of 2-oxazolidinone and 30.0 g of 1,2-dichloro-4-nitrobenzene in 200 ml of dimethylformamide. The mixture was stirred at 100° C. for 3 hours, then poured into water. The mixture was acidified with hydrochloric acid and extracted with ether. The solvent was evaporated from the extract under reduced pressure to give 1B, mp: 98°–100° C.

EXAMPLE 2

N'-(3-chloro-4-(5-methyl-2-oxo-3-oxazolidinyl)phenyl)-N,N-dimethylurea (2)

A solution of 19.85 g of 2-chloro-4-nitrophenyl isocyanate in 100 g of 2-chloro-1-propanol was heated by a steam bath for 10 minutes. The mixture then was cooled and diluted with 100 ml of ether and 100 ml of hexane, and the resulting mixture was filtered. The filter cake was washed with cold ether and dried to give 2-chloro-1-methylethyl (2-chloro-4-nitrophenyl)carbamate (2A), as a white solid, mp: 101°–103° C.

A solution of 5 g of potassium hydroxide in 10 ml of water was added to a stirred solution of 21.5 g of 2A in 300 ml of methanol. The mixture was heated for 0.5 hour by a steam bath and concentrated to dryness under reduced pressure. The residue was diluted with water; the mixture was acidified with hydrochloric acid and extracted with ether. The extract was dried and the solvent was evaporated under reduced pressure. Trituration of the residue with hexane gave 3-(2-chloro-4-nitrophenyl)-5-methyl-2-oxazolidinone (2B), as a solid, mp: 73°–75° C.

A solution of 16.5 g of 2B and 0.5 g of 10% palladium-on-carbon catalyst in 200 ml of tetrahydrofuran was treated with hydrogen in a Parr shaker, giving 3-(4-amino-2-chlorophenyl)-5-methyl-2-oxazolidinone (2C), as a white solid, mp: 140°–141° C.

3.6 g of 2C was added to a solution of 25 g of phosgene in 200 ml of toluene. The mixture was refluxed for one hour, then was held at room temperature for 12 hours. Excess phosgene and toluene were removed under reduced pressure. The residue (an oil) was added to a solution of an excess of dimethylamine in ether, to give 2, as a white solid, mp: 188°–190° C.

EXAMPLE 3

N'-(3-chloro-4-(2-oxo-3-oxazolidinyl)phenyl)-N-methyl-N-(2-propenyloxy)urea (3)

100 g of N-hydroxyurethane and 80.3 g of allyl chloride were added, at 20° C., to a solution of 53.8 g of potassium hydroxide in 750 ml of ethanol. The mixture was stirred and refluxed (80° C.) for 4 hours, then was cooled to 25° C. and filtered. The solvent was evaporated from the filtrate and the residue, an oil, was distilled, 51°–55° C., 0.2 Torr., to give ethyl (2-propenyloxy)carbamate, 3A, as a colorless oil.

264 g of anhydrous potassium carbonate and 271.2 g of methyl iodide were added to a solution of 59.2 g of 3A in 900 ml of acetone. The mixture was stirred and refluxed for 12 hours, then was cooled and filtered. The solvent was evaporated from the extract under reduced pressure and the residue was extracted with ether. The extract was washed with water, dried and distilled to give ethyl 2-methyl-2-propenyloxycarbamate, 3B, bp: 52°–59° C., 2.0 Torr.

3B was added to a solution of potassium hydroxide in aqueous methanol (1/9 v/v). The mixture was refluxed for 16 hours, cooled to 5° C. and acidified with concentrated hydrochloric acid. The resulting solution was concentrated to dryness; the residue was dissolved in the minimum amount of water; the solution was made alkaline with aqueous sodium hydroxide and extracted with ether. The ether was evaporated from the extract and the residue was distilled to give N-(2-propenyloxy)-methanamine, 3C, as a colorless liquid, bp: 92°–95° C., 760 Torr.

4.8 g of 1B was reduced with hydrogen in a Parr shaker (Raney nickel catalyst, tetrahydrofuran solvent, 50 p.s.i.g. hydrogen). A solution of the resulting aniline in ethyl acetate was treated with an excess of phosgene (5 hours at reflux). A solution of the resulting isocyanate in tetrahydrofuran was treated with 3.5 g of 3C (12 hours, room temperature). The resulting crude product was purified by silica gel chromatography to give 3, as a white solid, mp: 133°–135° C.

EXAMPLES 4-6

By the procedures described in Examples 1-3, the following further individual species of compounds of Formula I were prepared, the symbols being those of formula I:

| Ex. No. | Compound No. | R | $R^1$ | X | $R^2$ | $R^3$ | Melting Point (°C.) |
|---|---|---|---|---|---|---|---|
| 4 | 4 | H | H | Cl | —$CH_3$ | —$CH_3$ | 198–200 |
| 5 | 5 | —$CH_3$ | —$CH_3$ | Cl | —$CH_3$ | —$CH_3$ | 162–166 |
| 6 | 6 | —$CH_3$ | —$CH_3$ | Cl | —$CH_3$ | —$OCH_3$ | 126–128 |

Compounds of Formula I have been found to be useful for killing unwanted plants, being active with respect to both broad-leaved plants and grasses, and being effective when applied either preemergence (applied to the soil before the plants have sprouted) or postemergence (to the foliage of the growing plants).

Accordingly, the invention includes a method of killing unwanted plants which comprises applying to the locus an effective amount of a compound of Formula I. Likewise the invention also includes herbicidal compositions comprising a carrier or a surface-active agent, or both a carrier and a surface-active agent, and, as active ingredient, at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3-10% by weight of a dispersing agent, 15% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½-10% by weight of toxicant. Granules are usually prepared to have a size between 10 and 100 BS mesh (1.676-0.152 mm), and may be manufactured by agglomeration or impregnation techniques. Generally, granules will contain ½-25% by weight toxicant and 0-1% by weight of additives such as stabilizers, slow release modifiers and binding agents. Emulsifiable concentrates usually contain, in addition to the solvent and, when necessary, cosolvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, nonsedimenting, flowable product and usually contain 10-75% weight toxicant, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

Protection of a locus or area from undesirable plants is effected by applying a compound of Formula I, ordinarily in a composition of one of the aforementioned types, to the foliage of the plants or plant growth medium, e.g., soil in which the plant is growing or in which the seeds are present. The active compound, of course, is applied in an amount sufficient to exert the desired action.

The amount of compound of the invention to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

EXAMPLES OF HERBICIDAL ACTIVITY

The preemergence herbicidal activity of the compounds of the invention was evaluated by planting seeds of barnyard grass (*Echinochloa crus-galli*), garden cress (*Lepidium sativum*), downy brome (*Bromus tectorum*), velvetleaf (*Abutilon theophrasti*), yellow foxtail (*Setaria lutescens*), and sicklepod (*Cassia obtusifolia*) in test tubes, nominally measuring 25×200 millimeters, filled about three-quarters full of untreated soil, in each case covered on top with about 2.5 cubic centimeters of soil treated with the test compound at the rates of 0.1 and 1 milligram per tube designated in Table I at Rates I and II, respectively. The dosage of test compound were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amount of germination and growth in each tube were evaluated on a 0 to 9 scale, 0 rating indicating no effect, 9 death of the seedlings or no germination.

The postemergence activity of the compounds of this invention was evaluated by spraying 10-day old large crabgrass (*Digitaria sanguinalis*) plants, 13-day old redroot pigweed (*Amaranthus retroflexus*) plants, 6-day old downy brome plants (in four cases, 9-day old Johnson grass (*Sorghum halepense*) plants), 9-day old velvetleaf plants, 9-day old yellow foxtail plants and 9-day old sicklepod plants to runoff with a liquid formulation of the test compound at the rates of 2.4 milliliters of a 0.025% solution designated Rate I in Table I, and 2.4 milliliters of a 0.25% solution designated Rate II in Table I. The sprayed plants were held under conditions for 7 to 8 days and the effect of the test compound was then evaluated visually, the results being rated on the 0 to 9 scale described above.

The results of the test are summarized in Table I.

I claim:
1. A compound of the formula:

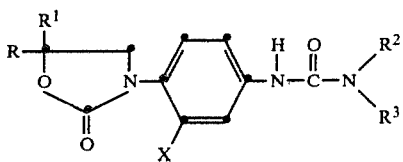

wherein R and $R^1$ each is hydrogen or lower alkyl, $R^2$ is lower alkyl and $R^3$ is lower alkyl, lower alkyloxy, or 2-propenyloxy, and X is middle halogen.

2. A herbicidal composition comprising a herbicidal amount of a compound of claim 1, and at least one surface-active agent or carrier therefor.

3. A method for killing unwanted plants at a locus which comprises applying to the locus to be protected a herbicidal amount of a compound of claim 1 or a composition containing it.

* * * * *

Table I

| | HERBICIDE SCREEN RESULTS | | | | | | | | | | | | | | | | | | | | | | | |
|---|---|---|---|---|---|---|---|---|---|---|---|---|---|---|---|---|---|---|---|---|---|---|---|---|
| | Preemergence (Soil) | | | | | | | | | | | | Postemergence (Foliar) | | | | | | | | | | | |
| | Barnyard Grass | | Garden Grass | | Downy Brome | | Velvet-leaf | | Yellow Foxtail | | Sickle-pod | | Crab-grass | | Pig-weed | | Downy Brome | | Velvet-leaf | | Yellow Foxtail | | Sickle-pod | |
| | | | | | | | | | | | Dosage | | | | | | | | | | | | | |
| Compound | I | II | I | II | I | II | I | II | I | II | I | II | I | II | I | II | I | II | I | II | I | II | I | II |
| 1 | 5 | 6 | 8 | 9 | 4 | 6 | 8 | 8 | 5 | 8 | 8 | 9 | 5 | 7 | 8 | 9 | 2 | 5 | 8 | 9 | 7 | 9 | 9 | 9 |
| 2 | 3 | 3 | 7 | 8 | 5 | 8 | 8 | 9 | 4 | 5 | 8 | 9 | 7 | 8 | 9 | 9 | 6 | 7 | 9 | 9 | 6 | 8 | 8 | 9 |
| 3 | 7 | 9 | 9 | 9 | 6 | 9 | 9 | 9 | 7 | 9 | 9 | 9 | 2 | 7 | 6 | 9 | 3(a) | 4 | 8 | 9 | 5 | 9 | 8 | 9 |
| 4 | 9 | 9 | 9 | 9 | 8 | 9 | 9 | 9 | 7 | 7 | 8 | 9 | 6 | 7 | 9 | 9 | 3(a) | 7 | 9 | 9 | 7 | 9 | 9 | 9 |
| 5 | 9 | 9 | 9 | 9 | 9 | 9 | 9 | 9 | 8 | 9 | 9 | 9 | 3 | 5 | 9 | 9 | 2(a) | 5 | 9 | 9 | 7 | 9 | 9 | 9 |
| 6 | 9 | 9 | 9 | 9 | 8 | 8 | 9 | 9 | 9 | 9 | 9 | 9 | 7 | 8 | 8 | 9 | 2(a) | 3 | 9 | 9 | 6 | 9 | 9 | 9 |

(a)Johnson Grass